(12) United States Patent
Amancha et al.

(10) Patent No.: US 9,370,518 B2
(45) Date of Patent: Jun. 21, 2016

(54) SILDENAFIL SUBLINGUAL SPRAY FORMULATION

(71) Applicant: Insys Pharma, Inc., Chandler, AZ (US)

(72) Inventors: Kiran Prakash Amancha, Chandler, AZ (US); Wesley Giron, Phoenix, AZ (US); Horng-Shin Li, Chandler, AZ (US); Venkat Goskonda, Phoenix, AZ (US); Thrimoorthy Potta, Phoenix, AZ (US)

(73) Assignee: INSYS DEVELOPMENT COMPANY, INC., Chandler, AZ (US)

( * ) Notice: Subject to any disclaimer, the term of this patent is extended or adjusted under 35 U.S.C. 154(b) by 0 days.

(21) Appl. No.: 14/536,057

(22) Filed: Nov. 7, 2014

(65) Prior Publication Data

US 2015/0133459 A1    May 14, 2015

Related U.S. Application Data

(60) Provisional application No. 61/901,829, filed on Nov. 8, 2013, provisional application No. 61/983,707, filed on Apr. 24, 2014.

(51) Int. Cl.
| | |
|---|---|
| *A61K 31/519* | (2006.01) |
| *A61K 47/12* | (2006.01) |
| *A61K 47/10* | (2006.01) |
| *A61K 47/26* | (2006.01) |
| *A61K 47/46* | (2006.01) |
| *A61K 9/00* | (2006.01) |
| *A61K 47/14* | (2006.01) |
| *A61K 9/08* | (2006.01) |

(52) U.S. Cl.
CPC .............. *A61K 31/519* (2013.01); *A61K 9/006* (2013.01); *A61K 9/08* (2013.01); *A61K 47/10* (2013.01); *A61K 47/12* (2013.01); *A61K 47/14* (2013.01); *A61K 47/26* (2013.01); *A61K 47/46* (2013.01)

(58) Field of Classification Search
CPC ..... A61K 31/519; A61K 9/006; A61K 47/12; A61K 47/10; A61K 47/26; A61K 47/46
See application file for complete search history.

(56) References Cited

U.S. PATENT DOCUMENTS

| | | | | |
|---|---|---|---|---|
| 7,125,564 B2 * | 10/2006 | Chen et al. | ...................... | 424/489 |
| 2007/0031349 A1 * | 2/2007 | Monteith et al. | ................ | 424/48 |
| 2009/0176834 A1 * | 7/2009 | Kottayil et al. | ............... | 514/329 |

OTHER PUBLICATIONS

Pereira Leonardo (quarta-feira, Sep. 5, 2012).*

* cited by examiner

*Primary Examiner* — Shirley V Gembeh
(74) *Attorney, Agent, or Firm* — Wood, Philips, Katz, Clark & Mortimer

(57) ABSTRACT

The invention is directed to sublingual spray formulations containing sildenafil. The invention is further directed to methods of treating male sexual dysfunction or pulmonary arterial hypertension by administering sublingual spray formulations containing sildenafil to patients in need of such treatments.

14 Claims, 1 Drawing Sheet

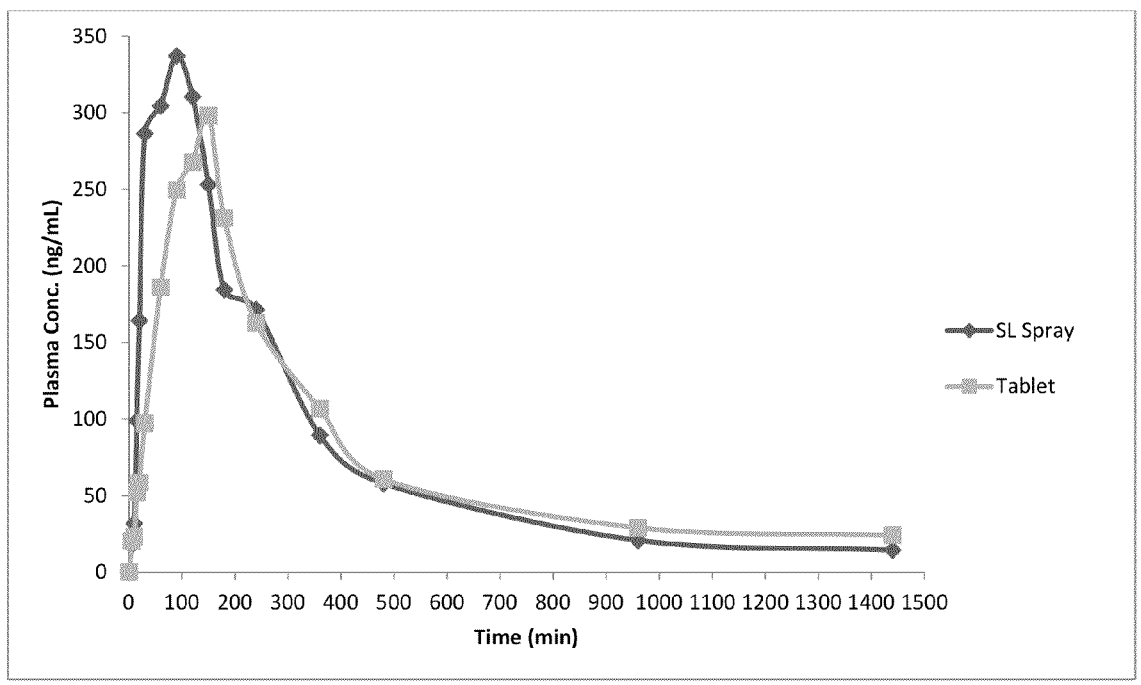

SILDENAFIL SUBLINGUAL SPRAY FORMULATION

PRIORITY

This application claims the benefit of U.S. Provisional Application Ser. Nos. 61/901,829 filed Nov. 8, 2013 and 61/983,707 filed Apr. 24, 2014, incorporated herein by reference.

FIELD OF THE INVENTION

The invention is directed to sublingual spray formulations containing sildenafil. The invention is further directed to methods for treating male erectile dysfunction or pulmonary arterial hypertension by administering sublingual spray formulations containing sildenafil to patients in need of such treatments.

BACKGROUND OF THE INVENTION

Sildenafil is a selective inhibitor of cyclic guanosine monophosphate (cGMP)-specific phosphodiesterase type 5 (PDE5). PDE5 is the predominant isozyme that metabolizes cGMP formed in the corpus cavernosum. Sildenafil is thought to enhance the effect of nitric oxide due to its inhibitory effect in the corpus cavernosum. The enhanced effect of nitric oxide therefore increases the cavernosal blood flow in the penis and lungs.

Sildenafil citrate is commercially available as a film coated tablet (Viagra®, available from Pfizer Inc.) for the treatment of erectile dysfunction. However, the reported bioavailability of this formulation is only 40%.

Sildenafil citrate is also commercially available in formulations for the treatment of pulmonary arterial hypertension. One such formulation is a film coated tablet (Revatio®, available from Pfizer Inc.).

"Sublingual" means "under the tongue" and refers to administration of a substance via the mouth in such a way that the substance is rapidly absorbed via the blood vessels under the tongue. A sublingual formulation is desirable because it bypasses hepatic first pass metabolic processes which provide better bioavailability, rapid onset of action, and higher patient compliance. Dysphagia (difficulty in swallowing) is common among in all ages of people and more common in geriatric patients. In terms of permeability, the sublingual area of oral cavity is more permeable than buccal area. Sublingual drug administration is applied in field of cardiovascular drugs, analgesics, steroids, enzymes and barbiturates.

U.S. Pat. No. 6,548,490 is directed to methods for treating erectile dysfunction including sublingually administering a composition that can include sildenafil. This method requires that the composition be in the form of a tablet, cream, ointment or paste. U.S. Pat. No. 8,133,903 discloses a method that includes administering up to 1.5 mg/kg/day of a PDE5 inhibitor, such as sildenafil, for not less than 45 days. This patent, however, also fails to disclose a fast acting oral spray formulation.

US Patent Application Publication No. 20130059854 discloses a method for mitigating erectile dysfunction by administering a composition orally that can include sildenafil. This formulation requires the use of sucrose fatty acid esters. U.S. Pat. No. 7,758,886 is directed to an aerosol composition including a poorly water-soluble active agent, such as sildenafil. This patent teaches that tyloxapol, polysorbates, vitamin E TPGS, or macrogol-hydroxystearates, and a phospholipid component, are required for administration. U.S. Pat. No. 6,585,958 discloses an aerosol formulation that may contain sildenafil. This formulation, however, requires a pressure-liquefied propellant mixture that includes dinitrogen monoxide and other components. In addition, US Patent Application Publication No. 20130143894 discloses a sildenafil oral spray formulation wherein the pH is from about 1.5 to less than 3.0. This application, however, teaches the use of a polar solvent such as propylene glycol and ethyl alcohol.

While there are various sildenafil formulations currently available, there is still a need in the art for an aqueous quick-onset sublingual spray formulation containing sildenafil.

BRIEF DESCRIPTION OF THE FIGURE

FIG. 1. A graph comparing the results from Example 8 below which compared a sublingual formulation of the present invention with an oral tablet formulation.

SUMMARY OF THE INVENTION

In one aspect, the present invention is directed to sublingual spray formulations comprising from about 0.1% w/w to about 30% w/w of sildenafil; from about 5% w/w to about 95% w/w of a pharmaceutically acceptable cosolvent selected from the group consisting of an alcohol, dehydrated alcohol, a glycol, a medium chain triglyceride and binary, ternary, or quaternary mixtures thereof; from about 1% w/w to about 40% w/w of an acidulent selected from the group consisting of malic acid, maleic acid, adipic acid, fumaric acid, tartaric acid, citric acid, palmitic acid and a pharmaceutically acceptable salt thereof; and from about 5% w/w to about 40% w/w water.

In another aspect, the present invention is directed to methods for treating male sexual dysfunction comprising administering the formulations of the present invention to a patient.

In a further aspect, the present invention is directed to methods for treating pulmonary arterial hypertension comprising administering the formulations of the present invention to a patient.

DETAILED DESCRIPTION

Applicants unexpectedly discovered sublingual sildenafil formulations that have improved bioavailability, a more rapid onset of action, and an improved storage stability.

In one embodiment, the invention is directed to sublingual spray formulations that comprise from about 0.1% w/w to about 30% w/w of sildenafil; from about 5% w/w to about 95% w/w of a pharmaceutically acceptable cosolvent selected from the group consisting of an alcohol, dehydrated alcohol, a glycol, a medium chain triglyceride and binary, ternary, or quaternary mixtures thereof; from about 1% w/w to about 40% w/w of an acidulent selected from the group consisting of malic acid, maleic acid, adipic acid, fumaric acid, tartaric acid, citric acid, palmitic acid and a pharmaceutically acceptable salt thereof; and from about 5% w/w to about 40% w/w water.

In a preferred embodiment, the formulations of the present invention are propellant free.

In another preferred embodiment, the formulation includes from about 10% w/w to about 30% w/w of sildenafil. In a more preferred embodiment, the formulation includes from about 14% w/w to about 21% w/w of sildenafil. Other most preferred embodiments include formulations with from about 18% w/w to about 21% w/w, from about 17% w/w to about 19% w/w, or from about 14% w/w to about 16% w/w of sildenafil.

Preferred sildenafil salts include citrate, hydrochloride, halide, sulfate, phosphate, acetate, maleate, succinate, ascorbate, carbonate, mesylate and lactate. One of skill in the art could use other pharmaceutically acceptable sildenafil salts in the formulations of the present invention. In a preferred embodiment, the formulation contains the pharmaceutically acceptable salt equivalent to from about 10% w/w to about 30% w/w of sildenafil. In a more preferred embodiment, the formulation contains the pharmaceutically acceptable salt equivalent to from about 14% w/w to about 21% w/w of sildenafil. Other most preferred embodiments include formulations which contain the pharmaceutically acceptable salt equivalent to from about 18% w/w to about 21% w/w, from about 17% w/w to about 19% w/w, or from about 14% w/w to about 16% w/w of sildenafil.

In a preferred embodiment, the formulation contains from about 20% w/w to about 35% w/w of water as the solvent.

In yet another embodiment, the formulations include a cosolvent. As used herein, a "cosolvent" refers to a solvent that works in conjunction with the water to dissolve the sildenafil. Other appropriate cosolvents known by those of skill in the art could also be added to formulations of the present invention. In a preferred embodiment, the formulations contain from about 10% w/w to about 40% w/w of the cosolvent. In more preferred embodiment, the formulations contain from about 15% w/w to about 30% w/w of the cosolvent. In a preferred embodiment, the cosolvent is dehydrated alcohol.

In one embodiment, the formulations of the present invention include a solubilizer or a surfactant or a stabilizer, a permeation enhancer, a preservative, an antioxidant, a sweetener, or a flavoring agent. In addition to these categories, excipients belonging to other appropriate categories known by those of skill in the art could also be added to formulations of the present invention As used herein, a "solubilizer or a surfactant or a stabilizer" refers to a compound that has at least one of these properties. In a preferred embodiment, the solubilizer or the surfactant or the stabilizer is nonionic surfactant such as polysorbate; sorbitan derivatives, polyvinylpyrrolidine and derivatives thereof, sodium lauryl sulfate, poloxamers, cremophor, lactic acid, Vitamin E TPGS or cyclodextrins and derivatives thereof. The solubilizer or the surfactant or the stabilizer can be a mixture of solubilizers and/or surfactants and/or stabilizers. Other appropriate solubilizers and/or surfactants and/or stabilizers known by those of skill in the art could also be added to formulations of the present invention. In a preferred embodiment, the formulations include from about 0.01% w/w to about 50% w/w of the solubilizer or surfactant or stabilizer. In a more preferred embodiment, the formulations contain from about 1% w/w to about 40% w/w of the solubilizer or surfactant or stabilizer.

In another embodiment, the pharmaceutically acceptable permeation enhancer is oleic acid, citric acid, cetylpyridinium chloride, glyceryl oleate, menthol, L-lysine, polysorbate-20, polysorbate-80, sodium lauryl sulfate, or sodium desoxycholate. The permeation enhancer can also be a mixture of permeation enhancers. Other appropriate permeation enhancers known by those of skill in the art could also be added to formulations of the present invention. In a preferred embodiment, the formulations contain from about 0.001% w/w to about 0.1% w/w of the permeation enhancer. In a more preferred embodiment, the formulations contain from about 0.005% w/w to about 0.05% w/w of the permeation enhancer.

In a further embodiment, the pharmaceutically acceptable antioxidant is butylated hydroxyanisole (BHA), butylated hydroxytoluene (BHT), ascorbic acid, methionine, sodium ascorbate, sodium thiosulfate, sodium bisulfite, sodium metabisulfite, ascorbyl palmitate or thioglycerol. The antioxidant could also be a mixture of antioxidants. Other appropriate antioxidants known by those of skill in art could also be added to formulations of the present invention. In a preferred embodiment, the formulations contain from about 0.001% w/w to about 1% w/w of the antioxidant. In a more preferred embodiment, the formulations contain from about 0.005% w/w to about 0.05% w/w of the antioxidant.

In yet another embodiment, the formulations of the present invention include a preservative that is methyl paraben, propyl paraben, sodium benzoate, benzoic acid, sorbic acid, or a mixture thereof. Other appropriate preservatives known by those of skill in art could also be added to formulations of the present invention. In a preferred embodiment, the formulations contain from about 0.001% w/w to about 1% w/w of the preservative. In a more preferred embodiment, the formulations contain from about 0.005% w/w to about 0.05% w/w of the preservative.

In one embodiment, the formulations of the present invention include a flavoring agent that is peppermint oil, blackberry, strawberry, raspberry, grape, lemon, lemon mint, cinnamon, menthol or a mixture thereof. Other appropriate flavoring agents known by those of skill in art could also be added to formulations of the present invention. In a preferred embodiment, the formulations contain from about 0.001% w/w to about 1% w/w of the flavoring agent. In a more preferred embodiment, the formulations contain from about 0.005% w/w to about 0.50% w/w of the flavoring agent. In an even more preferred embodiment, the formulation contains from about 0.05% w/w to about 0.20% w/w of the flavoring agent, preferably peppermint oil or strawberry flavoring. In most preferred embodiments, the formulations contain from about 0.08% w/w to about 0.2% w/w peppermint oil or strawberry flavoring.

In a further embodiment, the formulations of the present invention include acidulents such as malic acid, maleic acid, adipic acid, fumaric acid, tartaric acid, citric acid and palmitic acid or a pharmaceutically acceptable salt thereof, or a mixture thereof. In a preferred embodiment, the formulation contains malic acid. In a more preferred embodiment, the formulations contain from about 1% w/w to about 40% w/w of malic acid. In another preferred embodiment, the formulations contain from about 5% w/w to about 35% w/w of malic acid.

In another embodiment, the formulations of the present invention include a pharmaceutically acceptable sweetener such as sucralose, sucrose, fructose, acesulfame K, aspartame, sodium saccharin, stevia, xylitol, sorbitol, a Magnasweet® product (available from Mafco Worldwide Corporation, magnasweet is a registered trademark of Mafco Worldwide Corporation), or a mixture thereof. Magnasweet® products use the ammonium salt forms of crude and refined Glycyrrhizic Acid. Glycyrrhizic Acid is also available as a pure derivative in the sodium and potassium salt forms. One preferred Magnasweet® product is Magnasweet® 100.

In a preferred embodiment, the formulations contain from about 0.001% w/w to about 10% w/w of the sweetener. In a more preferred embodiment, the formulations contain from about 0.01% w/w to about 5% w/w of the sweetener. In an even more preferred embodiment, the formulations contain from about 0.005% w/w to about 2% w/w of the sweetener. In a most preferred embodiment, the formulations contain from about 0.05% w/w to about 1% w/w of the sweetener.

In a preferred embodiment, the invention is directed to sublingual spray formulations containing from about 0.1% w/w to about 25% w/w sildenafil, from about 5% w/w to about 40% w/w water, from 10% w/w to about 40% w/w alcohol, and from about 1% w/w to about 40% w/w malic acid. In a more preferred embodiment, the formulations contain from about 10% w/w to about 25% w/w sildenafil, from about 20% w/w to about 35% w/w water, from about 15% w/w to about 30% w/w alcohol, and from about 5% w/w to about 35% w/w malic acid. A most preferred formulation embodiment contains about 19% w/w to about 21% w/w sildenafil, from about 20% w/w to about 35% w/w water, from about 25% w/w to about 30% w/w alcohol, and about 30% w/w malic acid.

In another preferred embodiment, the formulation contains from about 10% w/w to about 25% w/w sildenafil, from about 20% w/w to about 35% w/w water, from about 15% w/w to about 30% w/w alcohol, and from about 5% w/w to about 35% w/w malic acid, from about 0.05% w/w to about 0.20% w/w sweetener, from about 0.005% w/w to about 0.02% w/w ammonium salt form of Glycyrrhizic Acid, and from about 0.10% w/w about 0.20% w/w of peppermint oil. Preferably, this formulation is propellant free.

In another preferred embodiment, the formulation contains from about 10% w/w to about 25% w/w sildenafil, from about 20% w/w to about 35% w/w water, from about 15% w/w to about 30% w/w alcohol, and from about 5% w/w to about 35% w/w malic acid, from about 0.05% w/w to about 0.20% w/w sweetener, from about 0.005% w/w to about 0.02% w/w ammonium salt form of Glycyrrhizic Acid, and from about 0.05% w/w about 0.12% w/w of strawberry flavoring. Preferably, this formulation is propellant free.

In another preferred embodiment, the formulation contains from about 14% w/w to about 21% w/w sildenafil, from about 25% w/w to about 35% w/w water, from about 25% w/w to about 30% w/w alcohol, and from about 25% w/w to about 35% w/w malic acid, from about 0.5% w/w to about 1.0% w/w sweetener, from about 0.001% w/w to about 0.1% w/w ammonium salt form of Glycyrrhizic Acid, and from about 0.10% w/w about 0.20% w/w of strawberry flavoring. Preferably, this formulation is propellant free. Preferably, the sildenafil is sildenafil base.

In another preferred embodiment, the formulation contains from about 18% w/w to about 21% w/w sildenafil, from about 25% w/w to about 35% w/w water, from about 25% w/w to about 30% w/w alcohol, and from about 25% w/w to about 35% w/w malic acid, from about 0.5% w/w to about 1.0% w/w sweetener, from about 0.001% w/w to about 0.1% w/w ammonium salt form of Glycyrrhizic Acid, and from about 0.10% w/w about 0.20% w/w of strawberry flavoring. Preferably, this formulation is propellant free. Preferably, the sildenafil is sildenafil base.

In another preferred embodiment, the formulation contains from about 17% w/w to about 19% w/w sildenafil, from about 25% w/w to about 35% w/w water, from about 25% w/w to about 30% w/w alcohol, and from about 25% w/w to about 35% w/w malic acid, from about 0.5% w/w to about 1.0% w/w sweetener, from about 0.001% w/w to about 0.1% w/w ammonium salt form of Glycyrrhizic Acid, and from about 0.10% w/w to about 0.20% w/w of strawberry flavoring. Preferably, this formulation is propellant free. Preferably, the sildenafil is sildenafil base.

In another preferred embodiment, the formulation contains from about 14% w/w to about 16% w/w sildenafil, from about 25% w/w to about 35% w/w water, from about 25% w/w to about 30% w/w alcohol, and from about 25% w/w to about 35% w/w malic acid, from about 0.5% w/w to about 1.0% w/w sweetener, from about 0.001% w/w to about 0.1% w/w ammonium salt form of Glycyrrhizic Acid, and from about 0.10% w/w to about 0.20% w/w of strawberry flavoring. Preferably, this formulation is propellant free. Preferably, the sildenafil is sildenafil base.

In another preferred embodiment, the formulation contains from about 18% w/w to about 21% w/w sildenafil, from about 25% w/w to about 35% w/w water, from about 25% w/w to about 30% w/w alcohol, and from about 25% w/w to about 35% w/w malic acid, from about 0.5% w/w to about 1.0% w/w sweetener, from about 0.001% w/w to about 0.1% w/w ammonium salt form of Glycyrrhizic Acid, and from about 0.10% w/w to about 0.20% w/w of peppermint oil. Preferably, this formulation is propellant free. Preferably, the sildenafil is sildenafil base.

In a further embodiment, the formulation contains from about from about 14% w/w to about 21% w/w sildenafil; from about 20% w/w to about 25% w/w dehydrated alcohol; from about 25% w/w to about 35% w/w malic acid; from about 0.5% w/w to about 1.0% w/w sweetener; from about 0.001% w/w to about 0.1% w/w ammonium salt form of Glycyrrhizic Acid; from about 0.10% w/w about 0.20% w/w flavoring agent; and from about 25% w/w to about 30% w/w water. Preferably, this formulation is propellant free. Preferably, the sildenafil is sildenafil base.

In another embodiment, the invention is directed to methods for treating sexual dysfunction in men comprising administering formulations of the present invention to a patient in need of such treatment.

In yet another embodiment, the invention is directed to methods for treating pulmonary arterial hypertension in humans comprising administering formulations of the present invention to a patient in need of such treatment.

In a preferred embodiment, administration of the sublingual formulation results in a mean $C_{max}$ of from about 380 to about 550 ng/ml, $T_{max}$ of from about 50 to about 110 minutes, and mean AUC0-t of from about 50,000 ng·min/mL to about 150,000 ng·min/mL. In a more preferred embodiment, administration of the sublingual formulation results in a mean $C_{max}$ of from about 400 to about 500 ng/ml, $T_{max}$ of from about 70 to about 100 minutes, and mean AUC0-t of from about 70,000 ng·min/mL to about 130,000 ng·min/mL. In a more preferred embodiment, administration of the sublingual formulation results in a mean $C_{max}$ of from about 450 to about 500 ng/ml, $T_{max}$ of from about 80 to about 90 minutes, and mean AUC0-t of from about 90,000 to about 120,000.

In a preferred embodiment, the formulations of the present invention do not discolor when stored at 40° C.±2° C. at 75%±5% relative humidity for six months.

In another preferred embodiment, the formulations of the present invention do not become contaminated with impurities when stored at 40° C.±2° C. at 75%±5% relative humidity for six months.

In yet another embodiment, the formulations of the present invention are capable of producing a droplet size distribution wherein the mean Dv(10) is from about 18 to about 32 microns during administration.

In a further embodiment, the formulations of the present invention are capable of producing a droplet size distribution wherein the mean Dv(50) is from about 50 to about 160 microns during administration.

In yet another embodiment, the formulations of the present invention are capable of producing a droplet size distribution wherein the mean Dv(90) is from about 400 to about 500 microns during administration.

In yet another embodiment, the formulations of the present invention are capable of producing a spray span ((Dv90−Dv10)/Dv50) of from about 3 to about 7.

As used herein, "sildenafil" refers to the base or a pharmaceutically acceptable salt, ester, derivative, or prodrug thereof.

As used herein, "propellant free" refers to a formulation that is not administered using compressed gas.

As used herein, "male sexual dysfunction" refers to erectile dysfunction or impotence. Erectile dysfunction and impotence are characterized by the inability to develop or maintain an erection of the penis during sexual activities.

As used herein, "pulmonary arterial hypertension" refers to the condition of having abnormally high blood pressure in the lungs.

As used herein, all numerical values relating to amounts, weights, and the like, that are defined as "about" each particular value is plus or minus 10%. For example, the phrase "about 10% w/w" is to be understood as "9% w/w to 11% w/w." Therefore, amounts within 10% of the claimed value are encompassed by the scope of the claims.

As used herein "% w/w" and "percent w/w" refer to the percent weight of the total formulation.

As used herein the term "effective amount" refers to the amount necessary to treat a patient in need thereof.

As used herein the term "patient" refers, but is not limited to, a person that is being treated for male sexual dysfunction or pulmonary arterial hypertension.

As used herein the term "pharmaceutically acceptable" refers to ingredients that are not biologically or otherwise undesirable in a sublingual dosage form.

The disclosed embodiments are simply exemplary embodiments of the inventive concepts disclosed herein and should not be considered as limiting, unless the claims expressly state otherwise.

The following examples are intended to illustrate the present invention and to teach one of ordinary skill in the art how to use the formulations of the invention. They are not intended to be limiting in any way.

EXAMPLES

Example 1

Preparation of a Sildenafil Sublingual Formulation

In order to prepare a sildenafil sublingual formulation, the components as indicated in "Table 1. The Components of Formulation 1" below were weighed. Then the water and alcohol were added to the malic acid. The solution was mixed until the malic acid was dissolved. The sildenafil was then added and mixed until a clear solution was formed. Accordingly, a 20% w/w sildenafil formulation was prepared for use as a sublingual formulation that does not require a propellant for administration.

TABLE 1

The Components of Formulation 1

| Formulation 1 | % w/w |
|---|---|
| Sildenafil Base | 20 |
| Malic Acid | 30 |
| Water | 27.5 |
| Alcohol | 22.5 |
| Total | 100 |

Example 2

Preparation of a Palatable Sildenafil Sublingual Formulation

Formulation 2 was prepared in a similar manner as was Formulation 1 using the components and amounts as indicated below in "Table 2. The Components of Formulation 2". Accordingly, a 20% w/w sildenafil formulation was prepared for use as a sublingual formulation that does not require a propellant for administration. Formulation 2 has a pleasant strawberry flavor.

TABLE 2

The Components of Formulation 2

| Formulation 2 | % w/w |
|---|---|
| Sildenafil | 20 |
| Malic acid | 30 |
| Strawberry | 0.08 |
| Sweetener | 0.05-0.20 |
| Magnasweet ® | 0.01 |
| Water | 27.5 |
| Dehydrated Alcohol | 20-25 |
| Total | 100 |

Example 3

Preparation of Another Palatable Sildenafil Sublingual Formulation

Formulation 3 was prepared in a similar manner as was Formulation 1 using the components and amounts as indicated below in "Table 3. The Components of Formulation 3". Accordingly, a 20% w/w sildenafil formulation was prepared for use as a sublingual formulation that does not require a propellant for administration. Formulation 3 also has a pleasant strawberry flavor.

TABLE 3

The Components of Formulation 3

| Formulation 3 | % w/w |
|---|---|
| Sildenafil Base | 20 |
| Malic acid | 30 |
| Strawberry type flavor | 0.08 |
| Sucralose | 0.6 |
| Magnasweet ® 100 | 0.01 |
| Purified water | 27.5 |
| Dehydrated Alcohol | 21.81 |
| Total | 100 |

Example 4

Preparation of Another Palatable Sildenafil Sublingual Formulation

Formulation 4 was prepared in a similar manner as was Formulation 1 using the components and amounts as indicated below in "Table 4. The Components of Formulation 4". Accordingly, an 18% w/w sildenafil formulation was prepared for use as a sublingual formulation that does not require a propellant for administration. Formulation 4 also has a pleasant strawberry flavor.

TABLE 4

The Components of Formulation 4

| Formulation 4 | % w/w |
|---|---|
| Sildenafil Base | 18 |
| Malic acid | 30 |
| Strawberry type flavor | 0.16 |
| Sucralose | 0.8 |
| Magnasweet ® 100 | 0.05 |
| Purified water | 27.5 |
| Dehydrated Alcohol | 23.49 |
| Total | 100 |

Example 5

Preparation of Another Palatable Sildenafil Sublingual Formulation

Formulation 5 was prepared in a similar manner as was Formulation 1 using the components and amounts as indicated below in "Table 5. The Components of Formulation 5". Accordingly, a 14.8% w/w sildenafil formulation was prepared for use as a sublingual formulation that does not require a propellant for administration. Formulation 5 also has a pleasant strawberry flavor.

TABLE 5

The Components of Formulation 5

| Formulation 5 | % w/w |
|---|---|
| Sildenafil Base | 14.84 |
| Malic acid | 26 |
| Strawberry type flavor | 0.16 |
| Sucralose | 0.8 |
| Magnasweet ® 100 | 0.05 |
| Purified water | 31.15 |
| Dehydrated Alcohol | 27.0 |
| Total | 100 |

Example 6

Preparation of Another Palatable Sildenafil Sublingual Formulation

Formulation 6 was prepared in a similar manner as was Formulation 1 using the components and amounts as indicated below in "Table 6. The Components of Formulation 6". Accordingly, a 20% w/w sildenafil formulation was prepared for use as a sublingual formulation that does not require a propellant for administration. Formulation 6 has a pleasant peppermint flavor.

TABLE 6

The Components of Formulation 6

| Formulation 6 | % w/w |
|---|---|
| Sildenafil | 20 |
| Malic acid | 30 |
| Peppermint oil | 0.15 |
| Sweetener | 0.05-0.20 |
| Magnasweet ® | 0.01 |
| Water | 27.5 |
| Dehydrated Alcohol | 20-25 |
| Total | 100 |

Example 7

Preparation of Another Palatable Sildenafil Sublingual Formulation

Formulation 7 was prepared in a similar manner as was Formulation 1 using the components and amounts as indicated below in "Table 7. The Components of Formulation 7". Accordingly, a 20% w/w sildenafil formulation was prepared for use as a sublingual formulation that does not require a propellant for administration. Formulation 7 also has a pleasant peppermint flavor.

TABLE 7

The Components of Formulation 7

| Formulation 7 | % w/w |
|---|---|
| Sildenafil Base | 20 |
| Malic acid | 30 |
| Peppermint oil | 0.15 |
| Sucralose | 0.8 |
| Magnasweet ® 100 | 0.01 |
| Purified water | 27.5 |
| Dehydrated Alcohol | 21.54 |
| Total | 100 |

Example 8

In order to determine the effectiveness of formulations of the present invention, Applicants performed a randomized, open label, two treatment, single dose, crossover pharmacokinetic, safety and tolerability study. Applicants compared the Formulation of Example 1 with a Pfizer Inc. sildenafil oral tablet in normal, healthy, adult human males after fasting. The Formulation of Example 1 was administered at a dose of 40 mg and the oral tablet was 50 mg.

The study was performed as follows. A total of 20 normal, healthy, adult, human male subjects were enrolled. The subjects received both formulations doses but during separate periods 7 days apart. Two subjects withdrew from the study because they missed giving plasma samples. The subjects were housed in a clinical facility at least 10 hours pre-dose until 24 hours after the dose in each period. The subjects fasted overnight for at least 10 hours before administration of the dose. The subjects received a standardized meal at about 4, 8, 12 and 24 hours after dosing in each period. The meal menu was the same during both periods. Drinking water was restricted from one hour pre-dose until one hour post-dose except for during administration of the dose.

Five ml blood samples were taken pre-dose and at 0, 5, 10, 15, 20, 30, 60, 90, 120, 150, 180, 240, 360, 480, 960 minutes and 24 hours post dose. Standard blood collection, sample separation techniques, and clinical safety measures were implemented. The concentration of sildenafil in plasma was quantified using a validated LC-MS/MS Bioanalytical method.

The pharmacokinetic analysis of oral and sublingual treatments indicated that sublingual administration achieved higher peak plasma concentrations at shorter times when compared to oral administration. This is significant in view of the lower dose of sublingual treatment (40 mg) when compared to the oral treatment (50 mg). The results can be seen below in Tables 8 and 9. The data is also illustrated in FIG. 1.

Specifically, the oral sildenafil tablets resulted in a mean $C_{max}$ (peak concentration) 367.7±181.2 (ng/ml), $T_{max}$ (time to peak concentration) of 120.0±47.2 minutes and mean AUC0-t (area under the curve) of 104268.2±205.0 ng·min/mL in the evaluated subjects. In the same subjects, sublingual administration resulted in a mean $C_{max}$ of 476.5±205.0, $T_{max}$ of 86.7±52.36 and AUC0-t of 106468.0±470020.0 ng·min/mL.

In summary, this study shows that the sublingual treatment resulted in higher blood plasma levels in less time than the oral tablet. The sublingual treatment had a mean $C_{max}$ that was 27% greater than the $C_{max}$ of the oral tablet. The sublingual treatment also had a mean $T_{max}$ that was 28% quicker than the $T_{max}$ of the oral tablet. This is especially significant because the dose of the sublingual treatment was lower than the dose of the tablet.

TABLE 8

Summary of Pharmacokinetic Parameters of Sildenafil 50 mg Oral Tablet

| Subject | $C_{max}$ (ng/ml) | $t_{1/2}$ (min) | K (min$^{-1}$) | $t_{max}$ (min) | AUC$_{0-t}$ ng·min/ml) | AUC$_{0-\infty}$ (ng·min/ml) | AUC0_t/ AUC0_inf) |
|---|---|---|---|---|---|---|---|
| 1 | 349.85 | 274.75 | 0.003 | 120.00 | 105273.15 | 110794.64 | 0.95 |
| 2 | 208.10 | 443.33 | 0.002 | 240.00 | 56721.68 | 63578.01 | 0.89 |
| 3 | 569.78 | 590.29 | 0.001 | 150.00 | 116335.50 | 139047.85 | 0.84 |
| 4 | 405.43 | 378.88 | 0.002 | 60.00 | 116460.73 | 125911.52 | 0.92 |
| 5 | 147.75 | 1326.72 | 0.001 | 90.00 | 53684.30 | 87276.03 | 0.62 |
| 7 | 117.56 | 855.06 | 0.001 | 120.00 | 35434.48 | 59625.07 | 0.59 |
| 8 | 521.21 | 200.55 | 0.004 | 150.00 | 161059.65 | 170165.11 | 0.95 |
| 9 | 256.88 | 274.09 | 0.003 | 150.00 | 69564.30 | 73566.10 | 0.95 |
| 10 | 243.44 | 304.16 | 0.002 | 120.00 | 60748.35 | 65377.76 | 0.93 |
| 11 | 824.67 | 2122.99 | 0.000 | 150.00 | 339488.53 | 711652.58 | 0.48 |
| 12 | 487.98 | 154.11 | 0.005 | 60.00 | 87031.80 | 89461.88 | 0.97 |
| 13 | 462.73 | 263.93 | 0.003 | 150.00 | 171441.33 | 175858.21 | 0.97 |
| 15 | 165.54 | 3835.97 | 0.000 | 30.00 | 37691.00 | 107808.42 | 0.35 |
| 16 | 382.81 | 241.41 | 0.003 | 90.00 | 69277.35 | 72986.62 | 0.95 |
| 17 | 480.44 | 79.74 | 0.009 | 150.00 | 89888.73 | 92960.27 | 0.97 |
| 18 | 219.17 | 777.07 | 0.001 | 120.00 | 84065.18 | 111789.43 | 0.75 |
| 19 | 484.78 | 177.59 | 0.004 | 120.00 | 143959.20 | 148406.98 | 0.97 |
| 20 | 290.52 | 522.81 | 0.001 | 90.00 | 78701.78 | 88665.45 | 0.89 |
| Mean | 367.70 | 712.41 | 0.00 | 120.00 | 104268.17 | 138607.33 | 0.83 |
| S.D | 181.20 | 927.24 | 0.00 | 47.15 | 70633.74 | 147300.76 | 0.19 |
| Median | | | | 120.00 | | | |

TABLE 9

Summary of Pharmacokinetic Parameters of Sildenafil 40 mg Sublingual Spray

| Subject | $C_{max}$ (ng/ml) | $t_{1/2}$ (min) | K (min$^{-1}$) | $t_{max}$ (min) | AUC$_{0-t}$ (ng·min/ml) | AUC$_{0-\infty}$ (ng·min/ml) | AUC0_t/ AUC0_inf) |
|---|---|---|---|---|---|---|---|
| 1 | 372.59 | 297.04 | 0.002 | 90.00 | 111969.60 | 119644.82 | 0.94 |
| 2 | 399.04 | 329.24 | 0.002 | 240.00 | 103625.10 | 108503.23 | 0.96 |
| 3 | 661.27 | 311.99 | 0.002 | 120.00 | 124567.83 | 130311.20 | 0.96 |
| 4 | 331.94 | 579.29 | 0.001 | 90.00 | 89711.90 | 103693.72 | 0.87 |
| 5 | 340.95 | 189.43 | 0.004 | 90.00 | 65644.80 | 68391.31 | 0.96 |
| 7 | 114.65 | 611.40 | 0.001 | 60.00 | 44479.03 | 58274.54 | 0.76 |
| 8 | 946.68 | 206.96 | 0.003 | 120.00 | 268848.55 | 272252.30 | 0.99 |
| 9 | 378.99 | 260.19 | 0.003 | 30.00 | 86764.93 | 90657.54 | 0.96 |
| 10 | 420.38 | 577.85 | 0.001 | 60.00 | 94829.10 | 103282.42 | 0.92 |
| 11 | 629.38 | 458.83 | 0.002 | 120.00 | 120786.00 | 127902.01 | 0.94 |
| 12 | 724.15 | 505.10 | 0.001 | 30.00 | 119628.30 | 127782.56 | 0.94 |
| 13 | 469.52 | 247.50 | 0.003 | 150.00 | 121625.85 | 125996.31 | 0.97 |
| 15 | 718.33 | 388.78 | 0.002 | 30.00 | 104626.23 | 117095.02 | 0.89 |
| 16 | 354.49 | 168.70 | 0.004 | 60.00 | 86651.23 | 89299.25 | 0.97 |
| 17 | 297.05 | 75.26 | 0.009 | 90.00 | 51349.65 | 52577.61 | 0.98 |
| 18 | 265.25 | 710.82 | 0.001 | 60.00 | 107723.95 | 139339.81 | 0.77 |
| 19 | 526.49 | 321.60 | 0.002 | 90.00 | 122503.08 | 129212.10 | 0.95 |
| 20 | 625.74 | 464.19 | 0.002 | 30.00 | 91088.50 | 99827.87 | 0.91 |
| Mean | 476.49 | 372.45 | 0.00 | 86.67 | 106467.98 | 114669.09 | 0.92 |
| ±S.D | 205.02 | 175.40 | 0.00 | 52.36 | 47019.60 | 46847.20 | 0.06 |
| Median | | | | 90.00 | | | |

Example 9

In order to determine the stability of Formulation 3, the formulation was subjected to standard stability testing. The results are below in "Table 10. Stability of Formulation 3".

TABLE 10

Stability of Formulation 3
Stability Data of Formulation 3 at 40° C. ± 2° C.
at 75% ± 5% relative humidity for six months

|  | RRT | T = 0 | 1 month | 2 months | 3 months | 6 months |
|---|---|---|---|---|---|---|
| Physical appearance |  | Clear to Yellow solution | Clear to Yellow solution | Clear to Yellow solution | Clear to Yellow solution | Clear to Yellow solution |
| Sildenafil Assay |  | 100.00% | 96.80% | 100.10% | 97.30% | 100.90% |
| Impurity A | 1.21 | BQL | BQL | BQL | BQL | BQL |
| Impurity B | 0.58 | ND | ND | ND | ND | ND |
| Impurity C | 0.5 | BQL | BQL | ND | BQL | BQL |
| Impurity D | 0.25 | BQL | BQL | BQL | BQL | BQL |
| Max Unspecified (%) |  | 0.00% | 0.00% | 0.00% | 0.00% | 0.00% |
| Total Impurities (%) |  | 0.00% | 0.00% | 0.00% | 0.00% | 0.00% |

As can be seen in Table 10, the formulation was stable by visual observation and by chemical analysis. "ND" means that the impurity was not detected and "BQL" means that the impurity was below a quantifiable limit. Relative retention time "RRT" is given for each impurity.

Example 10

In order to determine the spray profile of Formulation 4, it was subjected to standardized droplet testing. A challenge of creating a sildenafil sublingual spray formulation is that it must be capable of producing spray droplets that are over 10 microns in diameter. Spray droplets 10 microns or smaller could be inhaled into the lungs. The optimal particle size for sublingual spray droplets is from 20 to about 200 microns in diameter. It is desirable for the formulation to have droplet sizes near 20 because this increases the surface area and increased surface area exposure is one factor that contributes to a high bioavailability. Sublingual formulations should be able to maintain a consistent droplet size throughout its shelf life.

Droplet analysis was conducted using standard laser analysis procedures known by those of skill in the art. Droplet size distribution (Dv10, Dv50, Dv90, and Span were tested at two distances, 3 cm and 6 cm). Dv10 refers to droplet size for which 10% of the total volume is obtained; Dv50 refers to droplet size for which 50% of the total volume is obtained; Dv90 refers to droplet size for which 90% of the total volume is obtained; Span refers to distribution span (Dv90−Dv10)/Dv50; % RSD refers to the percent relative standard deviation. The results of these tests can be seen below in Tables 11 and 12. Applicants found during testing that formulations of the present invention yielded desirable droplet sizes for sublingual administration. The testing also revealed that the formulation dose remains consistent when administered with a spray pump.

TABLE 11

Spray Profile of Sildenafil SL Spray Formulation 4
Spray Distance: 3 cm

| Bottle | Actuation | $DV_{10}$ | $DV_{50}$ | $DV_{90}$ | Span |
|---|---|---|---|---|---|
| 1 | 1 | 28.36 | 111 | 391.5 | 3.271 |
|  | 2 | 33.58 | 135.5 | 507.7 | 3.5 |
|  | 3 | 29.97 | 210.8 | 540.3 | 2.421 |
|  | Average | 30.64 | 152.43 | 479.83 | 3.06 |
|  | Standard Deviation | 2.67 | 52.01 | 78.22 | 0.57 |
|  | % RSD | 8.73 | 34.12 | 16.30 | 18.55 |

TABLE 12

Spray Profile of Sildenafil SL Spray Formulation 4
Spray Distance: 6 cm

| Bottle | Actuation | $DV_{10}$ | $DV_{50}$ | $DV_{90}$ | Span |
|---|---|---|---|---|---|
| 1 | 1 | 35.89 | 115.5 | 341.1 | 2.642 |
|  | 2 | 28.26 | 82.89 | 388 | 4.341 |
|  | 3 | 24 | 57.57 | 510.9 | 8.458 |
|  | Average | 29.38 | 85.32 | 413.33 | 5.15 |
|  | Standard Deviation | 6.02 | 29.04 | 87.69 | 2.99 |
|  | % RSD | 20.50 | 34.04 | 21.22 | 58.10 |

Example 11

In order to determine the spray profile of Formulation 5, it was subjected to standardized testing. The results of these tests can be seen below in Tables 13 and 14. Applicants found during testing that formulations of the present invention yielded desirable droplet sizes for sublingual administration. The testing also revealed that the formulation dose remains consistent when administered with a spray pump.

TABLE 13

Spray Profile of Sildenafil SL Spray Formulation 5
Spray Distance: 3 cm

| Bottle | Actuation | $DV_{10}$ | $DV_{50}$ | $DV_{90}$ | Span |
|---|---|---|---|---|---|
| 1 | 1 | 18.39 | 58.11 | 429.8 | 7.079 |
|   | 2 | 19.07 | 64.47 | 449.9 | 6.682 |
|   | 3 | 21.1 | 150.2 | 579.8 | 3.721 |
|   | Average | 19.52 | 90.93 | 486.50 | 5.83 |
|   | Standard Deviation | 1.41 | 51.43 | 81.42 | 1.83 |
|   | % RSD | 7.22 | 56.56 | 16.74 | 31.49 |

TABLE 15

Spray Profile of Sildenafil SL Spray Formulation 5
Spray Distance: 6 cm

| Bottle | Actuation | $DV_{10}$ | $DV_{50}$ | $DV_{90}$ | Span |
|---|---|---|---|---|---|
| 1 | 1 | 21.05 | 53.85 | 457.8 | 8.112 |
|   | 2 | 23.97 | 68.75 | 557.9 | 7.767 |
|   | 3 | 22.99 | 67.34 | 355.4 | 4.936 |
|   | Average | 22.67 | 63.31 | 457.03 | 6.94 |
|   | Standard Deviation | 1.49 | 8.23 | 101.25 | 1.74 |
|   | % RSD | 6.56 | 12.99 | 22.15 | 25.12 |

Example 12

In order to determine the stability of Formulation 7, the formulation was subjected to standard stability testing. The results are below in "Table 15. Stability of Formulation 7".

TABLE 15

Stability of Formulation 7
Stability Data of Formulation 7 at 40° C. ± 2° C. at 75% ± 5% relative humidity for six months

| | RRT | T = 0 | 1 month | 2 months | 3 months | 6 months |
|---|---|---|---|---|---|---|
| Physical appearance | | Clear to Yellow solution | Clear to Yellow solution | Clear to Yellow solution | Clear to Yellow solution | Clear to Yellow solution |
| Sildenafil Assay | | 100.00% | 102.40% | 101.20% | 99.10% | 100.00% |
| Impurity A | 1.21 | BQL | BQL | BQL | BQL | BQL |
| Impurity B | 0.58 | ND | BQL | BQL | BQL | BQL |
| Impurity C | 0.5 | BQL | BQL | BQL | BQL | BQL |
| Impurity D | 0.25 | BQL | BQL | BQL | BQL | BQL |
| Max Unspecified (%) | | 0.00% | 0.00% | 0.00% | 0.00% | 0.00% |
| Total Impurities (%) | 0.50% | 0.00% | 0.00% | 0.00% | 0.00% | 0.00% |

As can be seen in Table 15, the formulation was stable by visual observation and by chemical analysis.

The invention claimed is:

1. A sublingual spray formulation comprising:
   a. about 0.1% w/w to about 30% w/w sildenafil;
   b. about 5% w/w to about 95% w/w of a pharmaceutically acceptable cosolvent selected from the group consisting of an alcohol, dehydrated alcohol, a glycol, a medium chain triglyceride and binary, ternary, or quaternary mixtures thereof;
   c. about 1% w/w to about 40% w/w of malic acid; and
   d. about 5% w/w to about 40% w/w water.
2. The formulation of claim 1 wherein the alcohol is dehydrated alcohol.
3. The formulation of claim 1 wherein the sildenafil is a pharmaceutically acceptable salt selected from the group consisting of citrate, hydrochloride, halide, sulfate, phosphate, acetate, maleate, succinate, ascorbate, carbonate, mesylate and lactate.
4. The formulation of claim 1 further comprising a pharmaceutically acceptable solubilizer and/or surfactant and/or stabilizer; and/or permeation enhancer; and/or antioxidant; and/or preservative; and/or flavoring agent; and/or sweetener.
5. The formulation of claim 4 wherein
   a. the solubilizer and/or surfactant and/or stabilizer is selected from the group consisting of polysorbate, sorbitan, polyvinylpyrrolidine, sodium lauryl sulfate, poloxamer, cremophor, lactic acid and cyclodextrin;
   b. the permeation enhancer is selected from the group consisting of oleic acid, citric acid, cetylpyridinium chloride, glyceryl oleate, menthol, L-lysine, polysorbate-20, polysorbate-80, sodium lauryl sulfate, sodium desoxycholate and a combination thereof;
   c. the antioxidant is selected from the group consisting of butylated hydroxyanisole (BHA), butylated hydroxytoluene (BHT), methionine, ascorbic acid, sodium ascorbate, sodium thiosulfate, sodium bisulfite, sodium metabisulfite, ascorbyl palmitate, thioglycerol, and a combination thereof;
   d. the preservative is selected from the group consisting of methyl paraben, propyl paraben, sodium benzoate, benzoic acid, sorbic acid, and a combination thereof;
   e. the flavoring agent is selected from the group consisting of peppermint oil, blackberry, strawberry, raspberry, grape, lemon, lemon mint, cinnamon, menthol, and a combination thereof; or
   f. the sweetener is selected from the group consisting of sucralose, sucrose, sorbitol, fructose, acesulfame K, aspartame, sodium saccharin, stevia, xylitol and ammonium salt of Glycyrrhizic Acid, and a combination thereof.
6. The formulation of claim 1 wherein administration results in a mean $C_{max}$ of about 380 to about 550 ng/ml, $T_{max}$ of about 50 to about 110 minutes, and mean AUC0-t of about 50,000 ng·min/mL to about 150,000 ng·min/mL.
7. The formulation of claim 1 wherein administration results in a mean $C_{max}$ of about 450 to about 500 ng/ml, $T_{max}$ of about 80 to about 90 minutes, and mean AUC0-t of about 90,000 ng·min/mL to about 120,000 ng·min/mL.
8. A method of treating pulmonary arterial hypertension in a human comprising administering the formulation of claim 1 to a patient in need thereof.

9. A method of treating sexual dysfunction in men comprising administering the formulation of claim 1 to a patient in need thereof.

10. A sublingual spray formulation comprising about 0.1% w/w to about 30% w/w sildenafil, about 5% w/w to about 40% w/w water, about 10% w/w to about 40% w/w denatured alcohol, and about 1% w/w to about 40% w/w malic acid.

11. The formulation of claim 10 wherein the formulation is propellant free.

12. The formulation of claim 10 comprising about 10% w/w to about 25% w/w sildenafil, about 20% w/w to about 35% w/w water, about 15% w/w to about 30% w/w denatured alcohol, and about 5% w/w to about 35% w/w malic acid.

13. The formulation of claim 12 further comprising about 0.05% w/w to about 0.20% w/w sweetener, about 0.005% w/w to about 1% w/w Glycyrrhizic Acid as the ammonium salt, and about 0.05% w/w to about 0.20% w/w of a flavoring agent selected from the group consisting of peppermint oil and strawberry.

14. A sublingual spray formulation comprising:
   a. about 14% w/w to about 21% w/w sildenafil;
   b. about 20% w/w to about 25% w/w dehydrated alcohol;
   c. about 25% w/w to about 35% w/w malic acid;
   d. about 0.5% w/w to about 1.0% w/w sweetener;
   e. about 0.001% w/w to about 0.1% w/w ammonium salt form of Glycyrrhizic Acid;
   f. about 0.10% w/w about 0.20% w/w flavoring agent; and
   g. about 25% w/w to about 30% w/w water.

* * * * *